(12) United States Patent
Kim et al.

(10) Patent No.: US 11,541,145 B2
(45) Date of Patent: Jan. 3, 2023

(54) FLUID TREATMENT APPARATUS

(71) Applicant: SEOUL VIOSYS CO., LTD., Ansan-si (KR)

(72) Inventors: Ji Won Kim, Ansan-si (KR); Jae Hak Jeong, Ansan-si (KR); Jong Man Kim, Ansan-si (KR); Sang Chul Shin, Ansan-si (KR); Si Ho Yu, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 281 days.

(21) Appl. No.: 16/629,843

(22) PCT Filed: Jul. 13, 2018

(86) PCT No.: PCT/KR2018/007939
§ 371 (c)(1),
(2) Date: Jan. 9, 2020

(87) PCT Pub. No.: WO2019/013578
PCT Pub. Date: Jan. 17, 2019

(65) Prior Publication Data
US 2021/0077652 A1   Mar. 18, 2021

(30) Foreign Application Priority Data
Jul. 13, 2017   (KR) .................... 10-2017-0089147

(51) Int. Cl.
*A61L 9/20* (2006.01)
*B01D 53/88* (2006.01)
*B60H 3/06* (2006.01)
*F24F 3/16* (2021.01)
*F24F 13/08* (2006.01)

(52) U.S. Cl.
CPC ............ *A61L 9/205* (2013.01); *B01D 53/885* (2013.01); *B60H 3/06* (2013.01); *F24F 3/16* (2013.01);
(Continued)

(58) Field of Classification Search
CPC .............................. A61L 9/205; B01D 53/885
See application file for complete search history.

(56) References Cited

U.S. PATENT DOCUMENTS 3,853,519 A * 12/1974 York, Jr. ............ B01D 46/0006
55/513
2007/0218828 A1   9/2007 Baik
(Continued)

FOREIGN PATENT DOCUMENTS

JP   2005-147457   6/2005
JP   3154670        10/2009
(Continued)

OTHER PUBLICATIONS

International Search Report dated Oct. 18, 2018, in International Application No. PCT/KR2018/007939 (with English Translation).
(Continued)

*Primary Examiner* — Kevin Joyner
(74) *Attorney, Agent, or Firm* — H.C. Park & Associates, PLC

(57) ABSTRACT

A fluid treatment apparatus including a photocatalyst filter having a first surface and a second surface, a light source unit spaced apart from the photocatalyst filter to provide light to the first surface, a housing including an inlet, an outlet, and a flow path formed between the photocatalyst filter and the light source, and a guide member disposed at one side of the housing and including at least one slat to guide a movement direction of a fluid, in which the slat is inclined at least in a direction closer to the first surface of the photocatalyst filter along an advancing direction of the flow path when an air flow rate of the fluid has a first value, and in a direction away from the first surface of the photocatalyst filter along the advancing direction when the air flow rate of the fluid is greater than the first value.

19 Claims, 13 Drawing Sheets

(52) U.S. Cl.
CPC ........... *F24F 13/08* (2013.01); *A61L 2209/12* (2013.01); *A61L 2209/14* (2013.01); *A61L 2209/15* (2013.01); *A61L 2209/16* (2013.01); *B01D 2255/20707* (2013.01); *B01D 2255/802* (2013.01); *B01D 2257/70* (2013.01); *B01D 2257/80* (2013.01); *B01D 2257/90* (2013.01); *B01D 2257/91* (2013.01)

(56) References Cited

U.S. PATENT DOCUMENTS

| | | | |
|---|---|---|---|
| 2016/0271550 A1* | 9/2016 | Law | B01D 46/442 |
| 2016/0325606 A1* | 11/2016 | Kim | A61L 9/205 |

FOREIGN PATENT DOCUMENTS

| | | |
|---|---|---|
| JP | 2011-143133 | 7/2011 |
| JP | 2014-233383 | 12/2014 |
| JP | 2015-222171 | 12/2015 |
| KR | 10-0701328 | 3/2007 |
| KR | 10-2012-0075798 | 7/2012 |
| KR | 10-2015-0062564 | 6/2015 |

OTHER PUBLICATIONS

Korean Office Action dated Nov. 30, 2021, issued to Korean Patent Application No. 10-2017-0089147 (with English Translation).

* cited by examiner

FLUID TREATMENT APPARATUS

CROSS-REFERENCE TO RELATED APPLICATIONS

This application is a National Stage Entry of International Application No. PCT/KR2018/007939, filed on Jul. 13, 2018, and claims priority from and the benefit of Korean Patent Application No. 10-2017-0089147, filed on Jul. 13, 2017, each of which is hereby incorporated by reference for all purposes as if fully set forth herein.

BACKGROUND

Field

Exemplary embodiments of the invention relate generally to a fluid treatment apparatus and, more specifically, to a fluid treatment apparatus used in an air conditioner.

Discussion of the Background

A vehicle air conditioner is a device for cooling or heating a vehicle interior by cooling or heating air introduced from the outside into the vehicle interior, or air circulating in the vehicle interior. The vehicle air conditioner generally includes an evaporator for cooling the air and a heater core for heating the air.

Users spend much time in a vehicle that has a small and enclosed space, and air quality is becoming worse due to external environment, such as fine dusts. Accordingly, there are needs for sterilizing and purifying air that passes through the vehicle air conditioner.

The above information disclosed in this Background section is only for understanding of the background of the inventive concepts, and, therefore, it may contain information that does not constitute prior art.

SUMMARY

Fluid treatment apparatuses constructed according to exemplary embodiments of the invention are capable of providing high fluid treatment efficiency.

Additional features of the inventive concepts will be set forth in the description which follows, and in part will be apparent from the description, or may be learned by practice of the inventive concepts.

A fluid treatment apparatus according to an exemplary embodiment includes a photocatalyst filter, a light source unit spaced apart from the photocatalyst filter to provide light to the photocatalyst filter, a housing accommodating the photocatalyst filter and the light source unit, and a guide member disposed at one side of the housing to guide a movement direction of a fluid. The guide member guides the fluid to move in a direction parallel to or inclined with respect to a surface of the photocatalyst filter.

The housing may include an inlet and an outlet, and a flow path through which the fluid moves therein, and the flow path may be disposed between the photocatalyst filter and the light source unit.

The photocatalyst filter may include a first surface facing the flow path and a second surface opposite to the first surface.

The guide member may include at least one slat.

The slat may be parallel to or inclined with respect to the first surface when viewed in a cross-section.

The slat may be inclined in a direction away from the first surface along an advancing direction of the flow path when viewed in the cross-section.

The slat may be inclined in a direction closer to the first surface along the advancing direction of the flow path when viewed in the cross-section.

When an air flow rate of the fluid has a first value, the slat may be inclined in the direction closer to the first surface along the advancing direction of the flow path when viewed in the cross-section. The slat may be inclined in the direction away from the first surface along the advancing direction of the flow path when the air flow rate of the fluid is greater than the first value in the cross-section.

The slat may be provided in a plural number, and at least one of the slats may form an angle with the first surface that is different from those formed by the remaining slats with the first surface.

The slat may be concavely or convexly curved with respect to the first surface when viewed in the cross-section.

The fluid treatment apparatus may further include an angle adjusting member to adjust an angle of the slat with respect to the first surface.

The angle may be adjusted by the angle adjusting member depending on the air flow rate of the fluid introduced through the inlet.

The slat may be inclined in the direction closer to the first surface along the advancing direction of the flow path when the air flow rate of the fluid has the first value, and inclined in the direction away from the first surface along the advancing direction of the flow path when the air flow rate of the fluid is greater than the first value in the cross-section.

The slat may extend in one direction, a lengthwise direction of the slat may be perpendicular to a direction of the flow path, and a widthwise direction of the slat may be parallel to the direction of the flow path.

The lengthwise direction of the slat may be parallel to the first surface. The flow path may be parallel to or inclined with respect to the first surface.

The housing may include a ceiling portion on which the photocatalyst filter is mounted, a bottom portion on which the light source unit is mounted, and a sidewall portion connecting the ceiling portion and the bottom portion.

The sidewall portion of the housing may include an insertion groove into which the photocatalyst filter is slide-coupled.

The light source unit may include at least one light source to emit light having at least one wavelength band of an ultraviolet light and a visible light. The light source unit may emit light having an ultraviolet C wavelength band.

The fluid treatment apparatus may be mounted on an air conditioner of an automobile, a refrigerator, or an air cleaner.

The guide member may be provided integrally with the housing without being separated from the housing.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
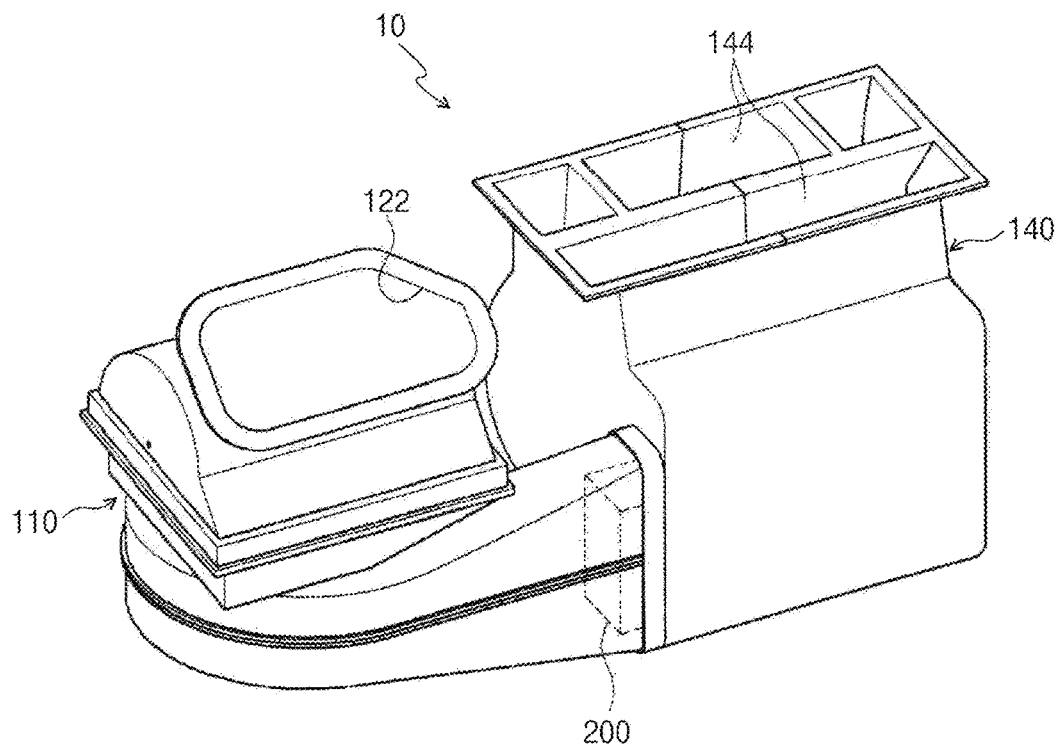
FIG. 1 is a perspective view showing a vehicle air conditioner according to an exemplary embodiment.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

A fluid treatment apparatus according to exemplary embodiments may be used in various air conditioners of vehicles, refrigerators, and air purifiers. A fluid may include water or air, and the fluid treatment apparatus may refer to an apparatus for treating air, such as sterilization, purification, and deodorization. However, the inventive concepts are not limited thereto as long as the fluid treatment apparatus is capable of sterilizing, purifying, deodorizing a specific fluid. In addition, the fluid treatment apparatus according to an exemplary embodiment may be used not only in the air conditioner but also in other apparatus. Hereinafter, the fluid treatment apparatus according to exemplary embodiments will exemplarily be described as being used in an air conditioner of a vehicle to treat air.

Figure 2:
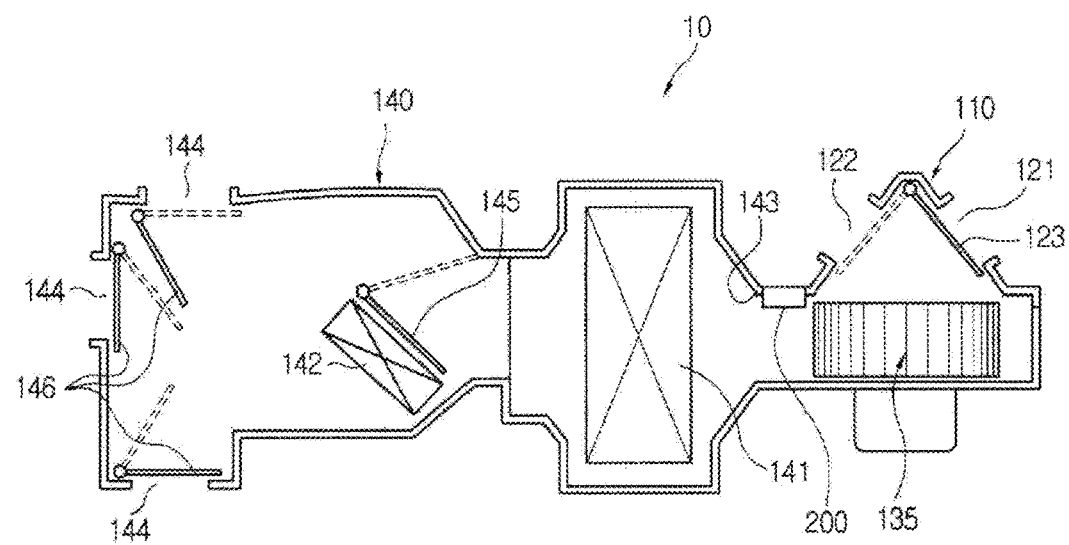
FIG. 2 is a cross-sectional view showing a vehicle air conditioner according to an exemplary embodiment.

FIGS. 1 and 2 are respectively a perspective view and a cross-sectional view showing a vehicle air conditioner according to an exemplary embodiment.

Referring to FIGS. 1 and 2, the vehicle air conditioner 10 according to an exemplary embodiment includes an air-conditioning case 140, an evaporator 141, a heater core 142, an air blower 110, a temperature control door 145, a plurality of mode doors 146, and a fluid treatment apparatus 200 including a photocatalyst filter.

The air-conditioning case 140 includes an air inlet 143 formed at an entrance thereof and a plurality of air outlets 144 formed at an exit thereof, and a flow path is formed in the air-conditioning case 140.

The evaporator 141 and the heater core 142 are sequentially installed in the air-conditioning case 140. The evaporator 141 and the heater core 142 are disposed on the flow path, and are spaced apart from each other by a predetermined distance. The evaporator 141 exchanges heat with air flowing through the flow path to cool the air. The evaporator 141 cools the air by flowing a cool refrigerant, and the heater core 142 heats the air by flowing a heated coolant. That is, the heater core 142 exchanges heat with the air flowing through the flow path to heat the air.

The air blower 110 blows air into the air-conditioning case 140. The air blower 110 is disposed adjacent to an internal air inlet 121 and an external air inlet 122. The internal air inlet 121 is connected to the inside of the vehicle, and the internal air flows therein. The external air inlet 122 is connected to the outside of the vehicle, and the external air flows therein.

The internal air inlet 121 and the external air inlet 122 are provided with an internal and external air switching door 123 for selectively opening and closing the internal air inlet 121 and the external air inlet 122. The internal and external air switching door 123 operates according to the setting of the vehicle occupant, which may control the external air or the internal air to be selectively introduced.

The air blower 110 includes a blower fan 135 for forcibly blowing the internal or external air to the air inlet 143 of the air-conditioning case 140.

The temperature control door 145 is installed between the evaporator 141 and the heater core 142. The temperature control door 145 adjusts an opening degree of a hot air passage that passes through the heater core 142 and a cold air passage that bypasses the heater core 142 to control an outlet temperature of the air. The mode doors 146 are respectively installed at the air outlets 144 and selectively open and close each air outlet 144 depending on various air conditioning modes.

The fluid treatment apparatus 200 is mounted on the vehicle air conditioner 100. The fluid treatment apparatus 200 sterilizes, purifies, and deodorizes the air supplied into the vehicle interior, and is disposed in front of the evaporator 141, thereby sterilizing, purifying, and deodorizing the air entering the evaporator 410.

Figure 3:
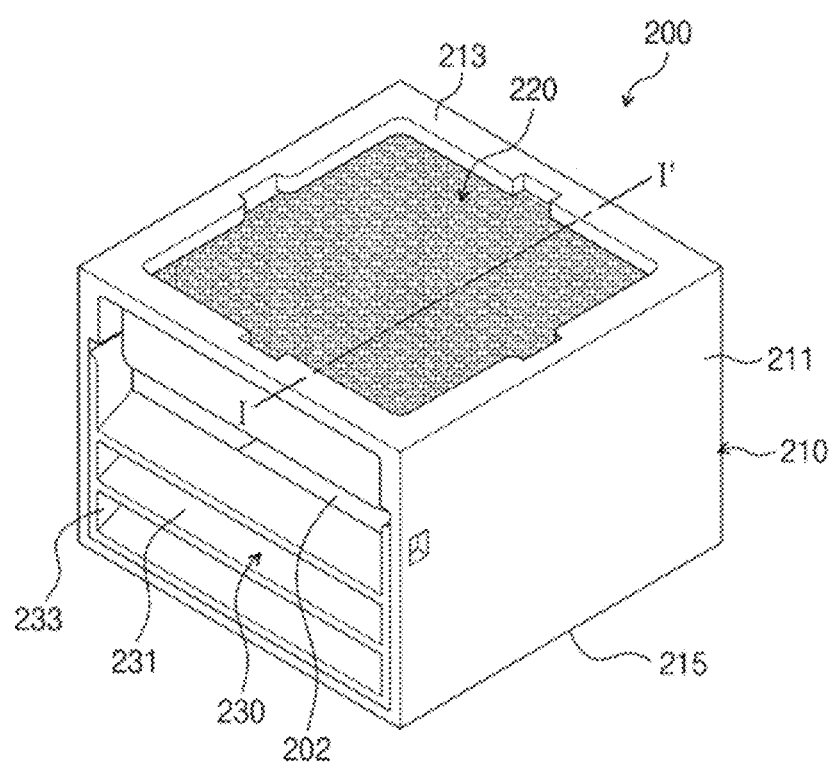
FIG. 3 is a perspective view showing a fluid treatment apparatus according to an exemplary embodiment.
Figure 4:
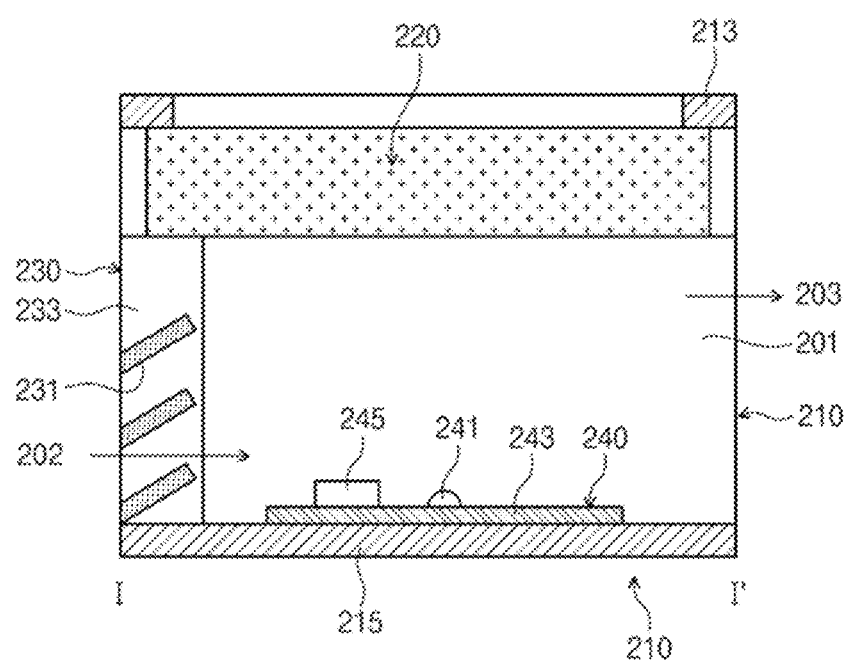
FIG. 4 is a cross-sectional view taken along line I-I' of FIG. 1.
Figure 5:
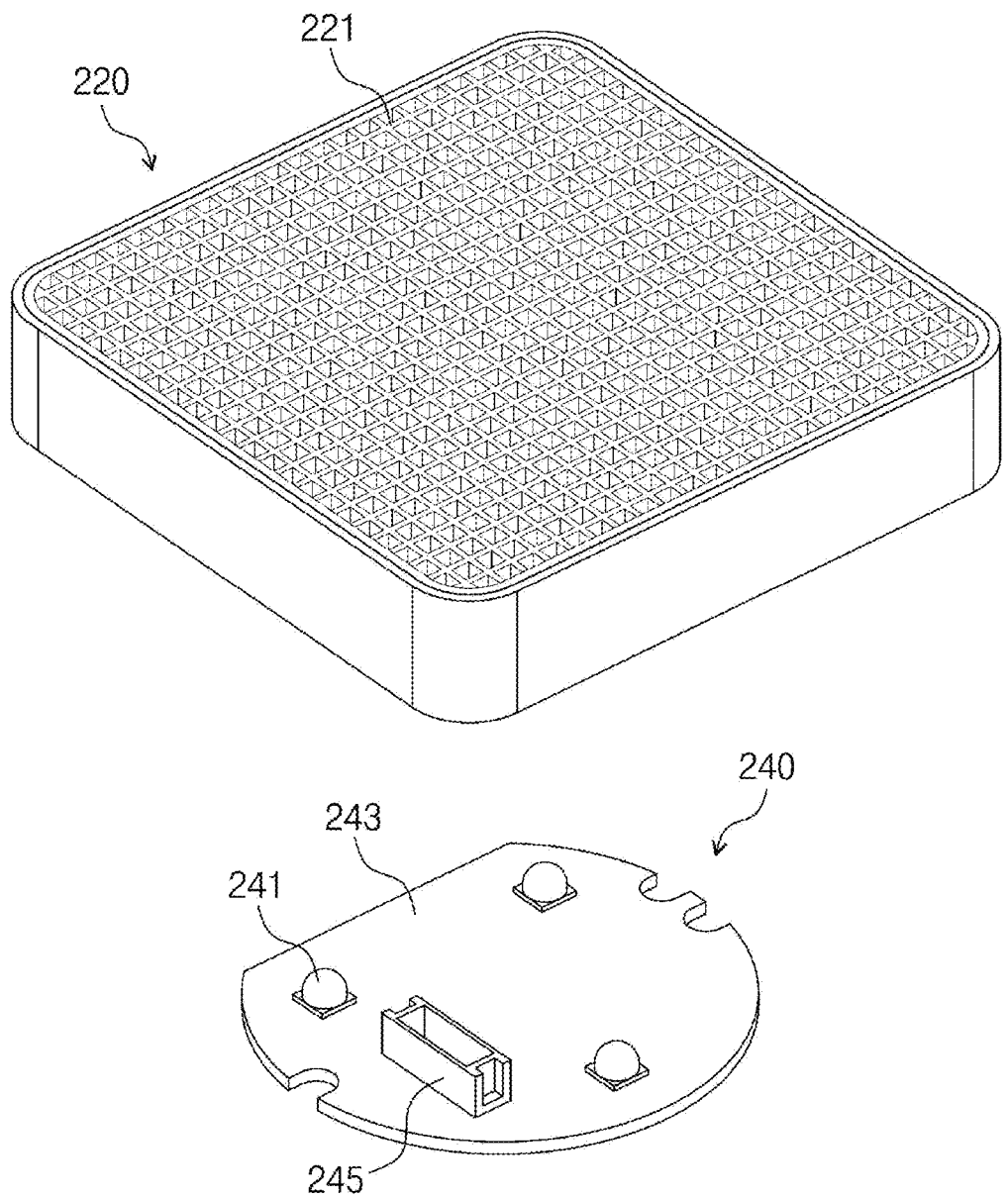
FIG. 5 is a perspective view showing a photocatalyst filter and a light source unit of a fluid treatment apparatus according to an exemplary embodiment.

FIG. 3 is a perspective view showing a fluid treatment apparatus according to an exemplary embodiment, and FIG. 4 is a cross-sectional view taken along line I-I' of FIG. 1. FIG. 5 is a perspective view showing a photocatalyst filter and a light source unit of a fluid treatment apparatus according to an exemplary embodiment.

Referring to FIGS. 3 to 5, the fluid treatment apparatus 200 according to an exemplary embodiment includes a housing 210 having an inner space 201, a photocatalyst filter 220 installed in the housing 210, a light source unit 240 providing light to the photocatalyst filter 220, and a guide member 230 guiding a direction of movement of the air.

The hosing 210 forms an appearance of the fluid treatment apparatus 200 and provides the inner space 201 in which the fluid, or the air in the illustrated exemplary embodiment, is treated. In some exemplary embodiments, however, additional case or component may be further provided outside the fluid treatment apparatus 200. In particular, as shown in FIGS. 1 and 2, when the fluid treatment apparatus 200 is used in the air conditioner, the housing 210 may be used as an internal component of the air conditioner.

The housing 210 is provided with an inlet 202 through which the air flows in, which is defined at one side of the housing 210, and an outlet 203 through which the air flows out, which is defined at the other side of the housing 210.

The housing 210 provides the inner space 201, and the flow path of air from the inlet 202 to the outlet 203 is formed in the inner space 201.

The housing 210 includes a ceiling portion 213 on which the photocatalyst filter 220 is mounted, a bottom portion 215 on which the light source unit 240 is mounted, and a sidewall portion 211 connecting the ceiling portion 213 and the bottom portion 215.

The ceiling portion 213, the sidewall portion 211, and the bottom portion 215 may be connected to each other, and form substantially a rectangular pipe shape whose both ends are opened. The opened ends respectively correspond to the inlet 202 and the outlet 203. The ceiling portion 213 may have a plate shape that is not opened, and may have an opening in some areas thereof. In the illustrated exemplary embodiment, the opening is formed through the ceiling portion 213, however, the ceiling portion 213 is not limited thereto.

Hereinafter, when the inlet 202, the inner space 201, and the outlet 203 are arranged along a straight line, a direction in which the inlet 202 is located will be referred to as a forward direction, a direction in which the outlet 203 is located will be referred to as a backward direction, a direction in which the ceiling 213 is located will be referred to as an upward direction, and a direction in which the bottom portion 215 is located will be referred to as a downward direction. However, these terms are relative terms, and in some exemplary embodiments, actual directions thereof may be set differently depending on mounting directions.

The air flowing through the inlet 202 and the outlet 203 is an object that may be subject to the treatment, such as sterilization, purification, and deodorization. The object that may be subject to the treatment, such as sterilization, purification, and deodorization, may be changed depending on the application of the fluid treatment apparatus.

The inlet 202 may have a circular shape or an oval shape when viewed from a front side, however, the inventive concepts are not limited thereto. In some exemplary embodiments, the inlet 202 may have various shapes in cross-section, e.g., a polygonal shape like a quadrangular shape.

The housing 210 accommodates components, for example, the light source unit 240 and the photocatalyst filter 220, which treat the air introduced through the inlet 202. The light source unit 240 and the photocatalyst filter 220 will be described in more detail later.

The inlet 202 may be connected to the inner space 201 of the housing 210. The outlet 203 may be spaced apart from the inlet 202, and may be connected to the inner space 201 of the housing 210. The inner space 201 of the housing 210 serves as a flow path of the air introduced through the inlet 202 and discharged through the outlet 203.

The outlet 203 may have a circular shape or an oval shape similar to the inlet 202 when viewed from a rear side, however, the inventive concepts are not limited thereto. In some exemplary embodiments, the outlet 203 may have various shapes, e.g., a polygonal shape.

In the illustrated exemplary embodiment, the air moves to the inner space 201 through the inlet 202, and is discharged to other components of the air conditioner, for example, through the outlet 203. The inlet 202 and the outlet 203 may be arranged in a variety of forms, and a movement direction of the air, that is, the flow path may vary depending on their arrangement order. For example, the inlet 202, the inside of the housing 210, and the outlet 203 may be arranged along a straight line or along a curved line.

The light source unit 240 is disposed in the housing 210 and emits light. In the illustrated exemplary embodiment, a light source 241 is disposed on the bottom portion 215 of the housing 210.

The light source unit 240 is spaced apart from the photocatalyst filter 220 and provides light to the photocatalyst filter 220.

In the illustrated exemplary embodiment, the light source unit 240 may be disposed directly on an upper surface of the bottom portion 215, however, the inventive concepts are not limited thereto. More particularly, the light source unit 240 may not need to be in contact with the bottom portion 215 as long as the light source unit 240 is spaced apart from the photocatalyst filter 220 to provide light to the photocatalyst filter 220. For example, in some exemplary embodiments, the light source unit 240 may be connected to a separate connection member protruded from the bottom portion 215, the sidewall portion 211, or the ceiling portion 213.

Light emitted from the light source unit 240 may have various wavelength bands. For example, light emitted from the light source unit 240 may have a visible light wavelength band, an ultraviolet light wavelength band, or other wavelength bands.

According to an exemplary embodiment, the wavelength band of light emitted from the light source unit 240 may be set differently depending on a photocatalytic material applied to the photocatalyst filter 220 to be described later. For example, the light source unit 240 may emit light having a wavelength band that reacts with the photocatalyst material.

The light source unit 240 may emit light, in which a portion thereof has a wavelength band that corresponds to the photocatalytic material. For example, the light source unit 240 may emit light having the ultraviolet light wavelength band, and in this case, the light source unit 240 may emit light having the wavelength band from about 100 nanometers to about 420 nanometers, and may emit light having the wavelength band from about 240 nanometers to about 400 nanometers. In the illustrated exemplary embodiment, the light source unit 240 may emit light having the wavelength band from about 250 nanometers to about 285 nanometers and/or light having the wavelength band from about 280 nanometers to about 350 nanometers. In another exemplary embodiment, the light source unit 240 may emit light having the wavelength band of about 275 nanometers and/or light having the wavelength band of about 365 nanometers.

To emit the above-mentioned light, the light source unit 240 may include at least one light source 241 that emits light. The light source 241 is not particularly limited as long as the light source 241 emits light having the wavelength band that reacts with the photocatalytic material. For example, when the light source unit 240 emits light having the ultraviolet light wavelength band, various light sources 241 that emit the ultraviolet light may be used. According to an exemplary embodiment, the light source 241 may include a light emitting diode (LED) that emits ultraviolet light. In the illustrated exemplary embodiment, the light source unit 240 may emit light having a sterilizing function to minimize the growth of bacteria in addition to light having the above-described wavelength. For example, the light source unit 240 may emit light having a wavelength band of about 100 nm to about 280 nm, which is an ultraviolet C wavelength band. When the light source unit 240 emits lights in various wavelength bands, other light sources 241 well-known in the art may be used.

When the LED is used as the light source 241 of the light source unit 240, the light source 241 may be mounted on a substrate 243.

In an exemplary embodiment, the light source unit 240 may be provided as a surface light source 241 and/or a point light source 241. In the illustrated exemplary embodiment, the light source unit 240 is provided as the point light source 241, as shown in FIG. 4.

The light source unit 240 includes the substrate 243 and the light source 241 mounted on the substrate 243.

The substrate 243 may have a plate shape. The substrate 243 may be elongated in a predetermined direction, or may be provided in a variety of shapes, such as a circular shape, an oval shape, or a polygonal shape, on which the light source 241 is mounted.

At least one light source 241 may be arranged on at least one surface of the substrate 243. When the light source 241 is provided in a plural number, the light sources 241 may be arranged in various ways, such as being randomly arranged, being arranged to have a specific shape, being provided along a straight line, or being provided along a zigzag shape. In this case, the light source 241 may be disposed to irradiate light to a maximum area of the photocatalyst filter 220 as uniformly as possible.

When the light source 241 is provided in plural, each of the light sources 241 may emit light having the same wavelength band as each other, or may emit light having different wavelength bands from each other. For example, in an exemplary embodiment, each of the light sources 241 may emit light having the ultraviolet light wavelength band. According to another exemplary embodiment, some light sources 241 may emit a portion of the ultraviolet wavelength band, and the other light sources 241 may emit the other portion of the other wavelength band of the ultraviolet wavelength band. For example, some light sources 241 may emit light having the wavelength band from about 320 nm to about 400 nm, and the other light sources 241 may emit light having different wavelength band from the wavelength band from about 320 nm to about 400 nm. When the light sources 241 emit light having different wavelength bands from each other, the light sources 241 may be arranged in various shapes and orders.

However, the wavelength band of light emitted from the light source 241 is not limited to the above-described range. According to other exemplary embodiments, the light source 241 may emit light not only in the ultraviolet light wavelength band but also in the visible light wavelength band.

A connector 245 may be further disposed on the substrate 243 of the light source 241 to connect the light source 241 to a line. The line (e.g., a power line) may be connected to the light source unit 240 through the connector 245.

In the illustrated exemplary embodiment, the light source unit 240 may provide light in a direction to which the photocatalyst filter 220 is disposed, such as the upper direction. As shown in the figures, when the light sources 241 are disposed on one surface of the substrate 243, light is mainly emitted in a direction substantially vertical to the one surface on which the light sources 241 are disposed. However, the direction of light emitted from the light source unit 240 may be changed in various ways.

The photocatalyst filter 220 is mounted in the inner space 201 of the housing 210. The photocatalyst filter 220 is spaced apart from the light source unit 240, and is disposed at a side portion of the direction in which the air moves. In the illustrated exemplary embodiment, the photocatalyst filter 220 is mounted on the ceiling portion 213 of the housing 210. The shape of the photocatalyst filter 220 is not particularly limited as long as the photocatalyst filter 220 may be mounted on the ceiling portion 213 of the housing 210 and may receive sufficient light from the light source 241. In the illustrated exemplary embodiment, the photocatalyst filter 220 may be manufactured in a rectangular parallelepiped shape having a relatively wide upper and lower surfaces.

The photocatalyst filter 220 may be mounted in the housing 210, such that the upper surface of the photocatalyst filter 220 makes contact with the ceiling portion 213 or faces the ceiling portion 213 at a close distance. A coupling member may be provided at the photocatalyst filter 220 and/or the sidewall portion 211 of the housing 210 to mount the photocatalyst filter 220 in the inner space 201 of the housing 210. For example, an insertion groove or a protrusion may be provided at the sidewall portion 211 of the housing 210, such that the photocatalyst filter 220 is slide-coupled to the housing 210. Accordingly, the photocatalyst filter 220 may be inserted into the housing 210 or withdrawn from the housing 210 after being separately manufactured, and the photocatalyst filter 220 may be easily replaced as needed.

In the illustrated exemplary embodiment, the lower surface of the photocatalyst filter 220 faces the light source unit 240. Since the photocatalyst filter 220 is mounted on the ceiling portion 213 and the light source unit 240 is mounted on the bottom portion 215, the photocatalyst filter 220 and the light source unit 240 may be spaced apart from each other by a predetermined distance.

The flow path is formed between the photocatalyst filter 220 and the light source unit 240, and thus, the air moves between the photocatalyst filter 220 and the light source unit 240. In this case, the air does not move through the photocatalyst filter 220, but moves in a direction substantially parallel to the lower surface of the photocatalyst filter 220 when viewed as a whole, although the air may move in an inclined manner. More particularly, the lower surface of the photocatalyst filter 220 may be provided substantially parallel to the moving direction of the air, e.g., the flow path.

The photocatalyst filter 220 may have a structure that maximizes a contact area with air. For example, the photocatalyst filter 220 according to an exemplary embodiment may have a lattice shape, and each lattice may be provided with a plurality of openings 221 vertically penetrating the photocatalyst filter 220. However, the shape of the photocatalyst filter 220 is not limited thereto, and the photocatalyst filter 220 may have other structures as long as large contact area with air can be secured. In some exemplary embodiments, the photocatalyst filter 220 may include a plurality of pores formed therein, rather than the opening 221 vertically penetrating therethrough.

The photocatalyst filter 220 includes a photocatalyst that reacts with light emitted from the light source unit 240 to treat the air.

The photocatalyst may induce a catalytic reaction when light is irradiated thereto. The photocatalyst may react with light various wavelength bands depending on the material constituting the photocatalyst. According to an exemplary embodiment, the photocatalyst may include materials that cause a photocatalytic reaction with light in the ultraviolet light wavelength band. However, the inventive concepts are not limited thereto, and other photocatalysts having the same or similar mechanism may be used depending on light emitted from the light source 241.

The photocatalyst is activated by the ultraviolet light to cause a chemical reaction, and thus, various contaminants, bacteria, and the like in the air in contact with the photocatalyst may be decomposed through a redox reaction.

The photocatalyst causes a chemical reaction that produces electrons and holes when exposed to light having energy equal to or greater than the material's band gap. Accordingly, compounds in the air, such as water or organic substances, may be decomposed by hydroxyl radical and superoxide ion formed by the photocatalytic reactions. The hydroxyl radical is a substance with high oxidizing property that decomposes contaminants or kills germs in the air. As the photocatalyst material, titanium dioxide ($TiO_2$), zinc oxide (ZnO), tin dioxide ($SnO_2$), and the like may be used. Since holes and electrons generated on the surface of the photocatalyst have a very high recombination rate, there is a limit in using the holes and the electrons for a photochemical reaction. Accordingly, metals such as Pt, Ni, Mn, Ag, W, Cr, Mo, and Zn, or oxides thereof, may be added to delay the recombination rate of the holes and the electrons. When the recombination rate of the holes and the electrons is delayed, the possibility of the holes and the electrons contacting with the material to be oxidized and/or decomposed increases, thereby increasing reactivity. In addition, it is also possible to improve the performance by adding oxides to adjust a photocatalyst bandgap. The air may be sterilized, purified, and deodorized by using the photocatalytic reaction described above. In particular, the sterilization is a bactericidal or antimicrobial activity that destroys enzymes in bacterial cells and enzymes acting on respiratory system, and thus, the growth of bacteria and fungi may be prevented and their toxins may be decomposed.

In particular, according to an exemplary embodiment, titanium dioxide ($TiO_2$) may be used as the photocatalyst. When titanium dioxide is irradiated with an ultraviolet light having a wavelength band equal to or less than about 400 nm, superoxide radicals may be produced to decompose organic substances into harmless water and carbon dioxide. Titanium dioxide may be nanoparticles and may produce large amounts of superoxide radicals even when using a light source that has a relatively weak ultraviolet wavelength. Accordingly, titanium dioxide has excellent decomposability of the organic substance, continuous durability and stability against environmental changes, and a semi-permanent effect. In addition, the superoxide radicals generated in large amounts may remove various substances, such as unpleasant odors and bacteria, as well as the organic substance.

According to an exemplary embodiment, while the photocatalyst acts as a catalyst, the photocatalyst itself is not changed, and thus, the photocatalyst may be used semi-permanently, and effects may be semi-permanent as long as corresponding light is provided.

The shape of the photocatalyst filter 220 may be determined in consideration of the shape of the housing 210 and the position of the light source unit 240 to receive light from the light source unit 240 as much as possible. For example, in the illustrated exemplary embodiment, one photocatalyst filter 220 provided on the ceiling portion 213 is exemplarily shown, however, the inventive concepts are not limited thereto. For example, in some exemplary embodiments, the photocatalyst filter 220 may also be provided on the sidewall portion 211, as long as light from the light source 241 may be provided in a direction substantially parallel to the flow path. In addition, the shape and the size of the photocatalyst filter 220 may be determined depending on whether the photocatalyst filter 220 is able to be mounted on the housing 210, whether light from the light source unit 240 sufficiently reaches the photocatalyst filter 220, and whether the photocatalyst filter 220 is sufficiently in contact with the air in a direction substantially parallel to the flow path.

The guide member 230 is mounted on the forward direction of the housing 210, e.g., at the inlet 202, and guides the direction in which the air moves. The guide member 230 controls a directivity of the air, such that the air moving to the inside of the housing 210 from the inlet 202 travels in a certain direction. The guide member 230 may be detachably mounted on the housing 210.

The guide member 230 includes a slat 231 and a supporter 233 fixing the slat 231.

The slat 231 is provided in a plate shape that is elongated in one direction and has a predetermined width. The slat 231 is provided in a shape to cross the inlet 202 from side to side. A lengthwise direction, in which the slat 231 is elongated, may be substantially parallel to the bottom portion 215. A widthwise direction of the slat 231 may be differently set depending on a direction in which the air is guided by the slat 231.

The slat 231 may be provided in a single piece or provided in a plural number. Three slats 231 are exemplarily shown in figures, however, the inventive concepts are not limited to a particular number of the slats 231, as long as the slats 231 effectively guide the air. For example, one, two, four, or more slats 231 may be provided in consideration of the size of the inner space 201 of the housing 210, the size of the inlet 202, the amount or speed of the moving air, and the like.

The supporter 233 is coupled to the sidewall portion of the housing 210 to fix the slats 231. Both ends of the slats 231 are connected to the supporter 233. In the illustrated exemplary embodiment, the supporter 233 and the slats 231 may be integrally formed with each other without being separated from each other. A coupling member that is coupled to the bottom portion 215 and/or the sidewall portion 211 of the housing 210 may be provided to the supporter 233. The coupling member may be a hook, a slide groove, a protrusion, a screw, or the like.

According to an exemplary embodiment, the slat 231 is parallel to or inclined to the lower surface of the photocatalyst filter 220 when viewed from a cross-section perpendicular to the lengthwise direction of the slat 231. The movement direction of the air passing through the slat 231 is changed depending on a degree of inclination of the slat 231 with respect to the lower surface of the photocatalyst filter 220. The degree of inclination of the slat 231 may be set differently depending on the amount of air provided to the lower surface side of the photocatalyst filter 220 through the slat 231.

FIGS. 6 to 10 are cross-sectional views showing the slats 231 of the fluid treatment apparatuses according to exemplary embodiments. In FIGS. 6 to 10, for the convenience of explanation, other components, except for the photocatalyst filter 220, the light source 241, and three slats 231, are not illustrated.

Figure 6:
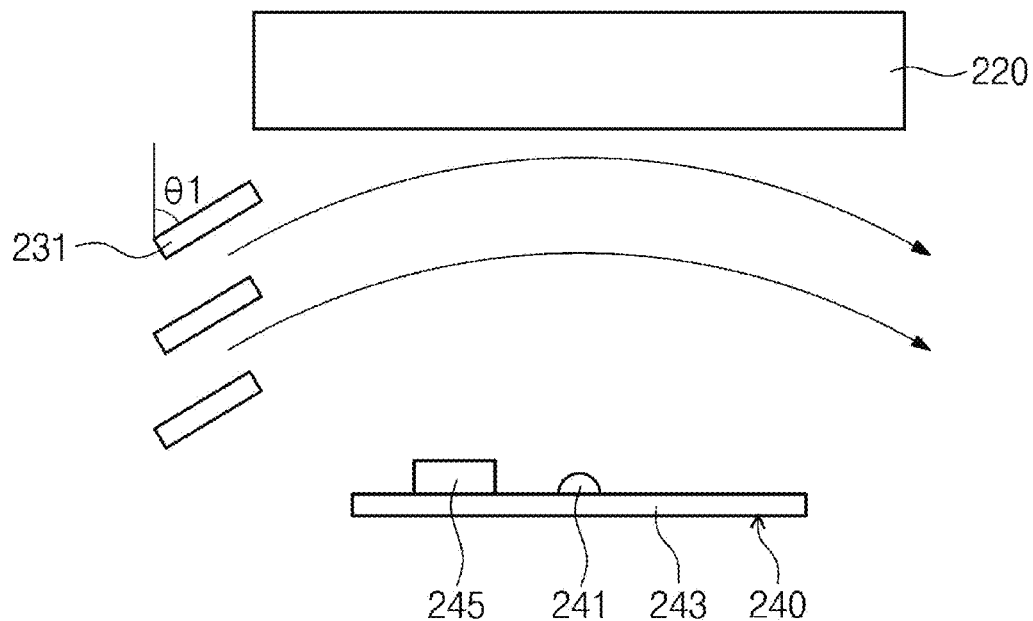
FIG. 6, FIG. 7, FIG. 8, FIG. 9, and FIG. 10 are cross-sectional views showing slats of fluid treatment apparatuses according to exemplary embodiments.

Referring to FIG. 6, the guide member 230 includes a plurality of slats 231, and the slats 231 are arranged in the upward direction. Each slat 231 is disposed to be inclined towards the lower surface of the photocatalyst filter 220.

When an angle between each slat 231 and the direction perpendicular to the lower surface of the photocatalyst filter 220 is referred to as a "first angle $\theta 1$", the first angle $\theta 1$ may be an acute angle. In particular, each slat 231 may be disposed in a direction to be close to the lower surface of the photocatalyst filter 220 along an advancing direction of the flow path when viewed from the cross-section.

Accordingly, the air introduced into the inner space 201 through the inlet and discharged through the outlet may move in a direction indicated by arrows. More particularly, the air flows in a direction that is gradually closer to the lower surface of the photocatalyst filter 220 on the inlet side. When the air approaches the lower surface of the photocatalyst filter 220, the movement direction of the air is bent due to a resistance effect of the lower surface of the photocatalyst filter 220. Then, the air flows in a direction away from the lower surface of the photocatalyst filter 220 and is discharged through the outlet.

The illustrated arrangement of the slats 231 may be applicable when an air flow rate is lower than a predetermined value, for example, about 1 m$^3$/min or less, or when the air flow rate is about 0.01 m$^3$/min or more and about 1 m$^3$/min or less. In this manner, when the air flow rate of the air making contact with the photocatalyst filter 220 is not sufficient, the possibility of the air coming into contact with the photocatalyst filter 220 may be increased by changing the movement direction of the air toward the photocatalyst filter 220 using the slats 231 according to the illustrated exemplary embodiment.

Figure 7:
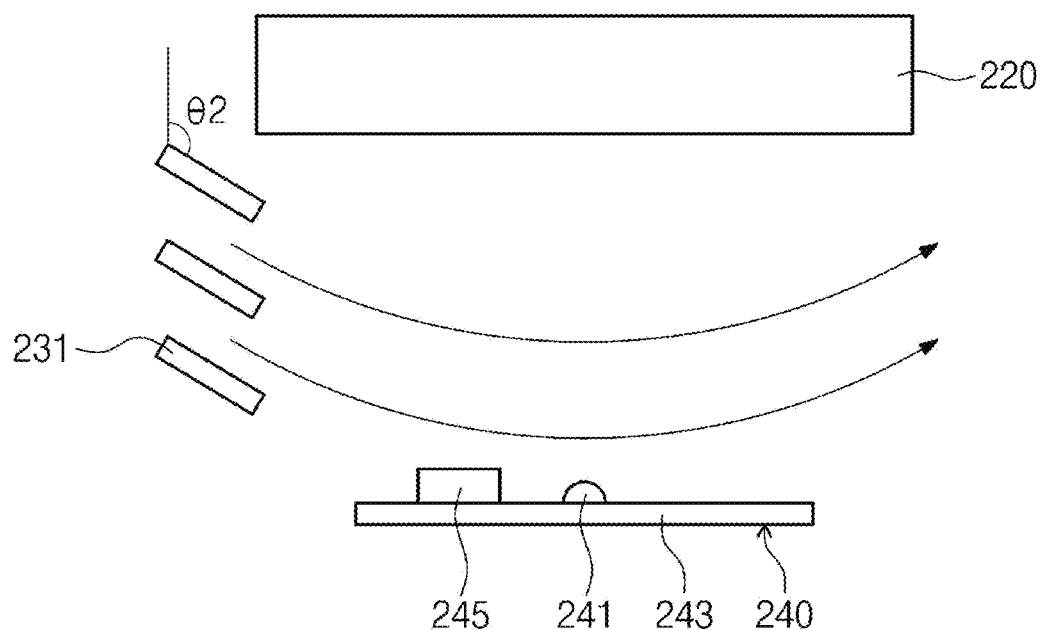

Referring to FIG. 7, the guide member 230 includes a plurality of slats 231, and the slats 231 are arranged in the downward direction. Each slat 231 is disposed to be inclined in a direction away from the lower surface of the photocatalyst filter 220.

When an angle between each slat 231 and the direction perpendicular to the lower surface of the photocatalyst filter 220 is referred to as a "second angle θ2", the second angle θ2 may be an obtuse angle. In particular, each slat 231 may be disposed in a direction away from the lower surface of the photocatalyst filter 220 along an advancing direction of the flow path when viewed from the cross-section.

Accordingly, the air introduced into the inner space 201 through the inlet and discharged through the outlet may move in a direction indicated by arrows. More particularly, the air flows in a direction away from the lower surface of the photocatalyst filter 220, e.g., a direction closer to the light source unit 240, on the inlet side. When the air approaches the upper surface of the light source unit 240, the movement direction of the air is bent due to a resistance effect of the upper surface of the light source unit 240. Then, the air flows in a direction away from the light source unit 240 and is discharged through the outlet.

The illustrated arrangement of the slats 231 may be applicable when an air flow rate is higher than a predetermined value, for example, about 1 m$^3$/min, or when the air flow rate exceeds about 1 m$^3$/min and about 81 m$^3$/min or less. When the air flow rate is greater than a predetermined value, the air may be discharged through the outlet without ensuring a sufficient reaction time with the photocatalyst filter 220. As such, the movement direction of the air according to the illustrated exemplary embodiment may be changed to a direction away from the photocatalyst filter 220 to ensure the sufficient reaction time, and thus, the time during which the air is in contact with the photocatalyst filter 220 may be increased.

According to exemplary embodiments, the slats 231 may be arranged in various other ways depending on the air flow rate of the air flowing through the flow path.

Figure 8:
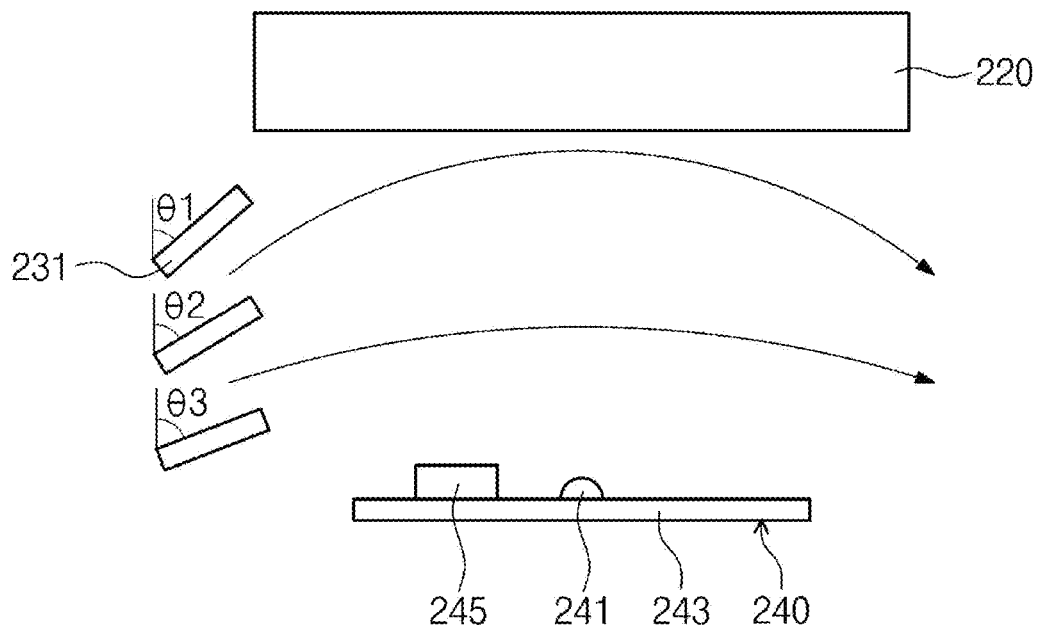

Referring to FIG. 8, each slat 231 may be disposed to be inclined to the lower surface of the photocatalyst filter 220 as shown in FIG. 6, however, the slats 231 may have different slopes with respect to the direction perpendicular to the lower surface of the photocatalyst filter 220. In particular, angles between the slats 231 and the direction perpendicular to the lower surface of the photocatalyst filter 220 may be different from each other in accordance with an arrangement order of the slats 231 from the photocatalyst filter 220. In this case, some slats 231 may have different angles from each other, and the other slats 231 may be arranged at the same angle as each other. In some exemplary embodiments, each of the slats 231 may be arranged to have different angles from each other.

When angles of the slats 231 sequentially arranged from the photocatalyst filter 220 with respect to the direction perpendicular to the lower surface of the photocatalyst filter 220 are referred to as first, second, and third angles θ1, θ2, and θ3, the first angle θ1 may be less than the second angle θ2, and the second angle θ2 may be less than the third angle θ3.

The arrangement of the slats 231 may be determined within a range capable of maximizing the contact time with the photocatalyst filter 220 according to the air flow rate of the air flowing through the flow path. In addition, when the air flow rate of the air introduced through the inlet is different depending on a height, the slats 231 that guide the air may also be arranged at different angles from each other.

Figure 9:
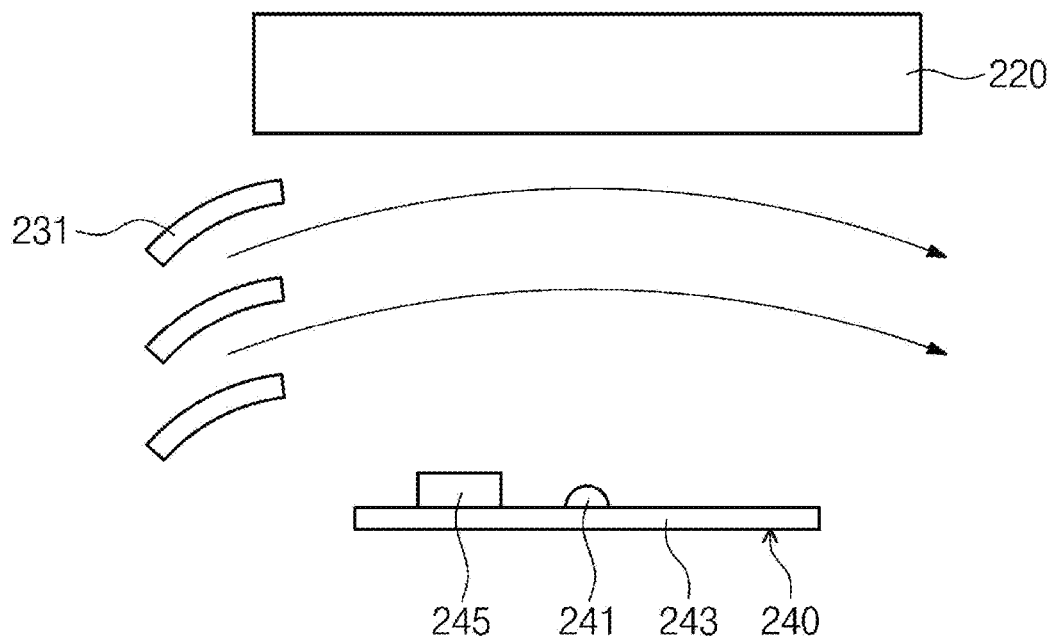

Referring to FIG. 9, the slats 231 may have a curved shape in a widthwise direction, rather than a flat plate shape. In FIG. 9, the slats 231 have a convexly-curved shape with respect to the bottom surface of the photocatalyst filter 220 when viewed in cross section. However, the inventive concepts are not limited thereto, and in some exemplary embodiments, the slats 231 may have a concavely-curved shape with respect to the bottom surface of the photocatalyst filter 220.

According to an exemplary embodiment, the guide member 230 may guide the air in various directions. For example, the slats 231 of the guide member 230 may form the flow path outside the photocatalyst filter 220 as well as between the photocatalyst filter 220 and the light source unit 240.

Figure 10:
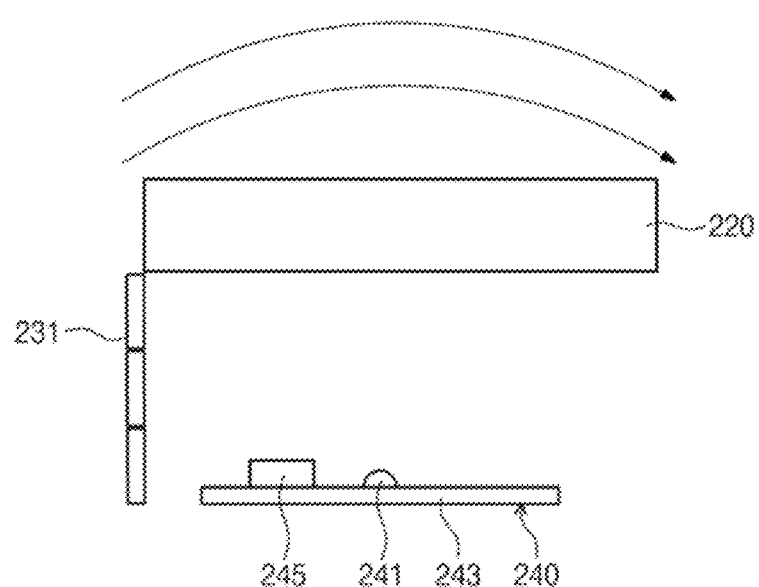

Referring to FIG. 10, when viewed in a cross-section perpendicular to a lengthwise direction of the slat 231 of the guide member 230, the slat 231 may be disposed perpendicular to the bottom surface of the photocatalyst filter 220. In the illustrated exemplary embodiment, when the slat 231 is disposed perpendicular to the bottom surface of the photocatalyst filter 220, the air inlet to the inner space of the housing 210 is closed by the slat 231. Accordingly, the air does not move to the inner space between the photocatalyst filter 220 and the light source unit 240. Instead, the air may flow above the photocatalyst filter 220. In this case, since the light source unit 240 is disposed under the photocatalyst filter 220, light emitted from the light source unit 240 is continuously provided to the photocatalyst filter 220. Since the photocatalyst filter 220 is provided with a plurality of openings defined vertically therethrough, the air flowing above the photocatalyst filter 220 may also be sterilized, purified, and deodorized.

As described above, the guide member 230 may be provided in various forms according to the air flow rate of the air. Accordingly, when the air flow rate of the air flowing into the inlet of the apparatus, such as a vehicle air conditioner, a refrigerator, etc., employing the fluid treatment apparatus according to an exemplary embodiment, is measured and the guide member having the slat 231 corresponding to the measured result is employed, effective sterilization, purification, and deodorization, and the like may be achieved. For example, when the air flow rate of the air flowing into the inlet in the air conditioner has a first value, the slats 231 inclined in the direction closer to the lower surface of the photocatalyst along the advancing direction of the flow path may be employed, and when the air flow rate of the air flowing into the inlet in the air conditioner has a second value greater than the first value, the slats 231 inclined in the direction away from the lower surface of the photocatalyst filter 220 along the advancing direction of the flow path may be employed, or the slats 231 disposed perpendicular to the lower surface of the photocatalyst filter 220 may be employed. The guide member 230 may be provided in an attachable and detachable form, and different guide members 230 may be attached to the fluid treatment apparatus depending on the air flow rate, thereby maximizing a fluid treatment efficiency.

According to an exemplary embodiment, the arrangement of the slats 231 may be changed by detaching and attaching the guide member 230 as described above. However, in other exemplary embodiments, an angle adjusting member that controls the angle of the slats 231 in the guide member 230 may be further included. The angle adjusting member may adjust the angle of the slats 231, and may have any structure of an angle adjusting member well-known in the art. The angle adjusting member may adjust the angle of the slats 231 in various ways in accordance with the air flow rate of the air flowing through the inlet.

Figure 11:
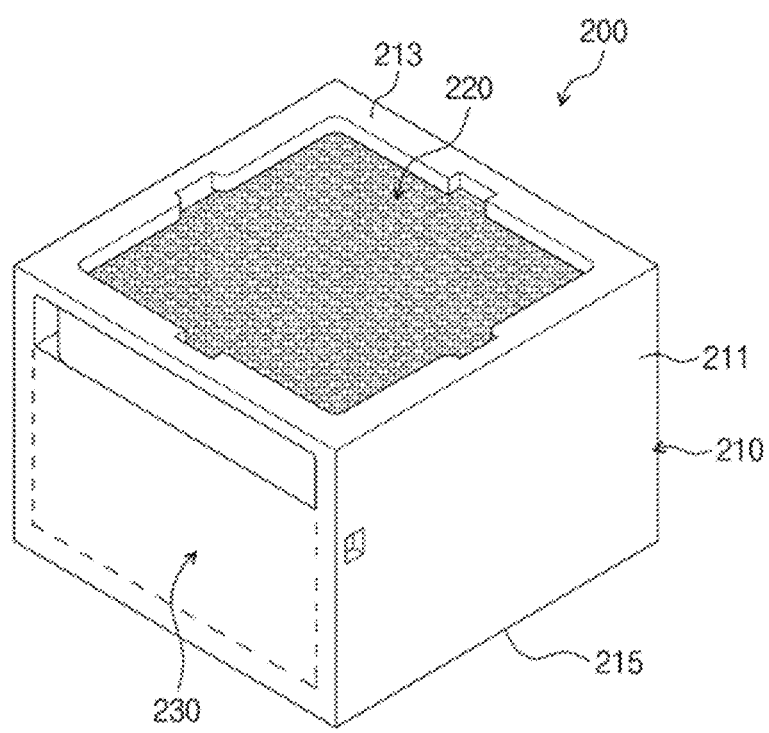
FIG. 11 is a perspective view showing a fluid treatment apparatus according to an exemplary embodiment.

The fluid treatment apparatus according to an exemplary embodiment may be changed in various forms depending on the shape of the slat or the advancing direction of the flow path. FIG. 11 is a perspective view showing a modified structure of the fluid treatment apparatus shown in FIG. 10.

Referring to FIG. 11, the slats of the guide member 230 have a shape similar to that shown in FIG. 10, except that the guide member 230 is integrally formed with the housing 210 without being separated. In particular, a separate slat that is vertically formed may not be provided, and the housing 210 may have a closed shape without the inlet. Although not shown in figures, the outlet may or may not be provided, and when the outlet is not provided, only an upper portion may be opened between the photocatalyst filter and the light source unit by the housing 210, and the sidewall portion 211 may have a closed shape. In addition, the housing 210 may be changed into other forms as long as the photocatalyst filter 220 is fixed and supported. For example, the ceiling portion 213 of the housing 210 may be changed such that the photocatalyst filter 220 is coupled to the housing 210 in a top-down manner.

In the fluid treatment apparatus according to the illustrated exemplary embodiment, the air does not flow between the photocatalyst filter 220 and the light source unit 240, similar to that shown in FIG. 10. Instead, the air may flow above the photocatalyst filter 220. In this case, since the light source unit 240 is disposed under the photocatalyst filter 220, light emitted from the light source unit 240 is continuously provided to the photocatalyst filter 220. Since the photocatalyst filter 220 is provided with a plurality of openings defined vertically therethrough, the air flowing above the photocatalyst filter 220 may also be sterilized, purified, and deodorized.

The fluid treatment apparatus according to the exemplary embodiments has the effect of sterilization, purification, and deodorization, which are optimized for the air flow rate. Hereinafter, an experimental example of removing a predetermined substance (e.g., ammonia, formaldehyde, and toluene) using a conventional fluid treatment apparatus and the fluid treatment apparatus according to the exemplary embodiments will be described.

Figure 12:
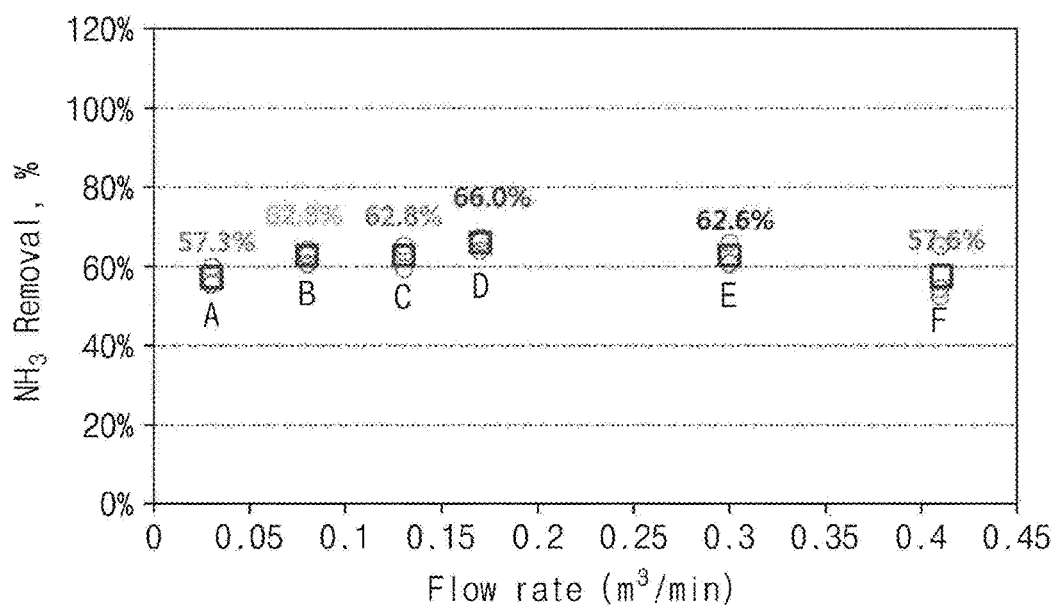
FIG. 12 is a graph showing an ammonia removal rate according to an air flow rate at low air flow rate conditions in a conventional fluid treatment apparatus.
Figure 13:
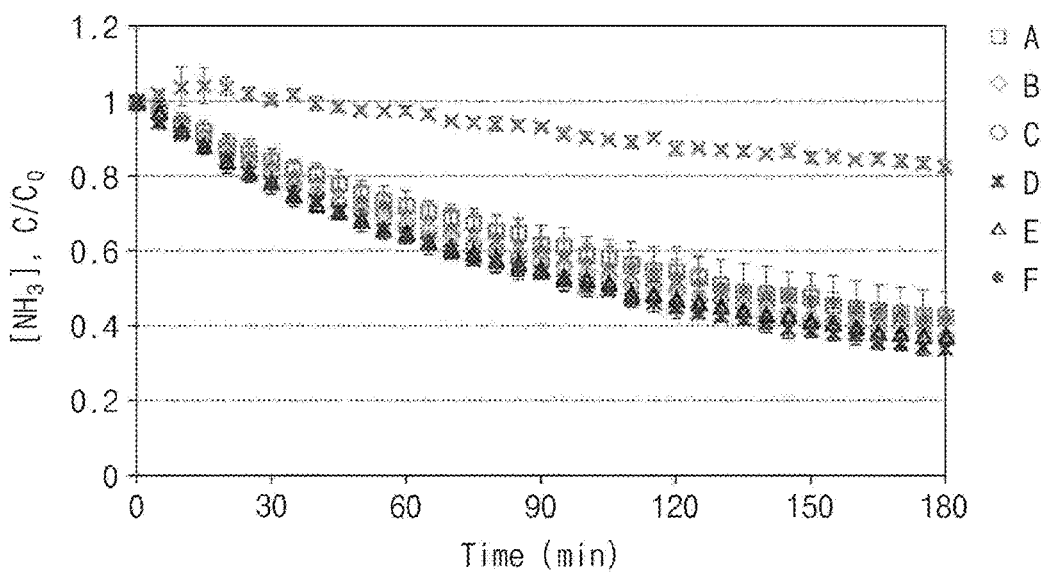
FIG. 13 is a graph showing an ammonia removal rate according to time at low air flow rate conditions in a conventional fluid treatment apparatus.

FIG. 12 is a graph showing an ammonia removal rate according to an air flow rate at low air flow rate conditions in a conventional fluid treatment apparatus, and FIG. 13 is a graph showing an ammonia removal rate according to time at low air flow rate conditions in a conventional fluid treatment apparatus.

The fluid treatment apparatus used in FIGS. 12 and 13 have an opened inlet and do not include a separate guide member. The conventional fluid treatment apparatus includes substantially the same components as those shown in FIG. 6, except for the inlet of the housing and the guide member. Experiments were performed in a chamber of 1 m$^3$. A distance between the photocatalyst filter and the light source unit was about 20 mm, and three light sources that emit light of a wavelength band of about 365 nm were used. An average intensity of the ultraviolet light was about 20.0 mW/cm$^2$, and a size of the photocatalyst filter was 55 mm×55 mm×10 mm. FIG. 12 shows a deodorization efficiency during about 3 hours.

The air flow rates of A, B, C, D, E, and F shown in FIGS. 12 and 13 corresponded to about 0.03 m$^3$/min, about 0.08 m$^3$/min, about 0.13 m$^3$/min, about 0.17 m$^3$/min, about 0.30 m$^3$/min, and about 0.41 m$^3$/min, respectively. Portions indicated by "X" in FIG. 13 show a case where the fluid treatment apparatus is not driven.

Referring to FIG. 12, when the conventional treatment apparatus was used at the low air flow rate conditions, there was no significant difference in the ammonia removal rate according to the air flow rate. More particularly, there was no significant relationship between the air flow rate and the ammonia removal rate at the low air flow rate conditions. In addition, referring to FIG. 13, when the conventional treatment apparatus was used at the low air flow rate conditions, the difference in removal efficiency according to the air flow rate was not large. However, since the removal efficiency of ammonia increased with the passage of time as shown in FIG. 13, it was confirmed that more fluid needs to stay in the fluid treatment apparatus for a long time.

Figure 14:
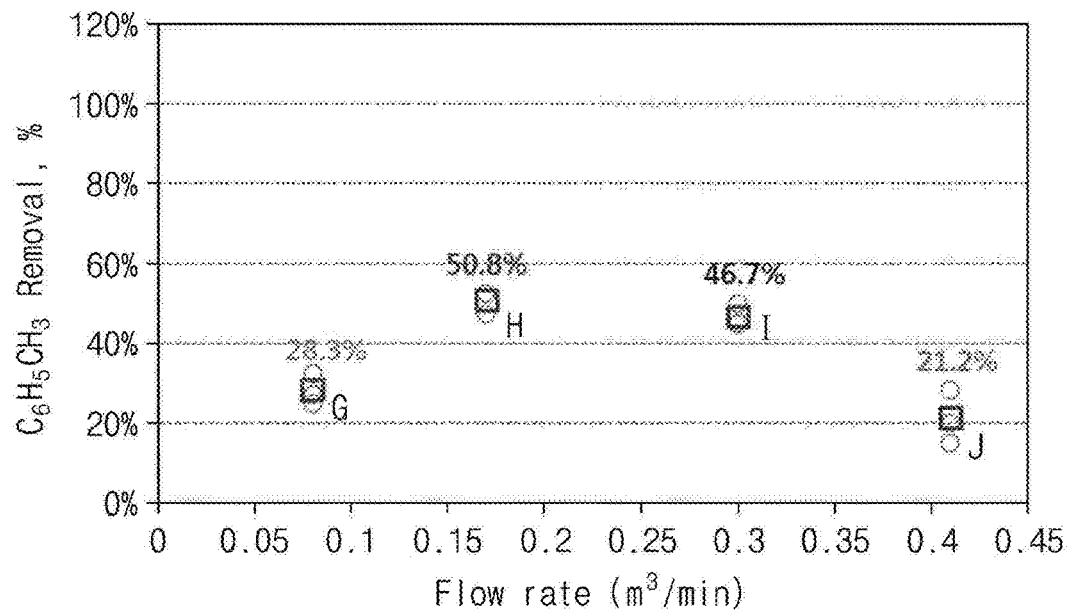
FIG. 14 is a graph showing a toluene removal rate according to an air flow rate at low air flow rate conditions in a conventional fluid treatment apparatus.
Figure 15:
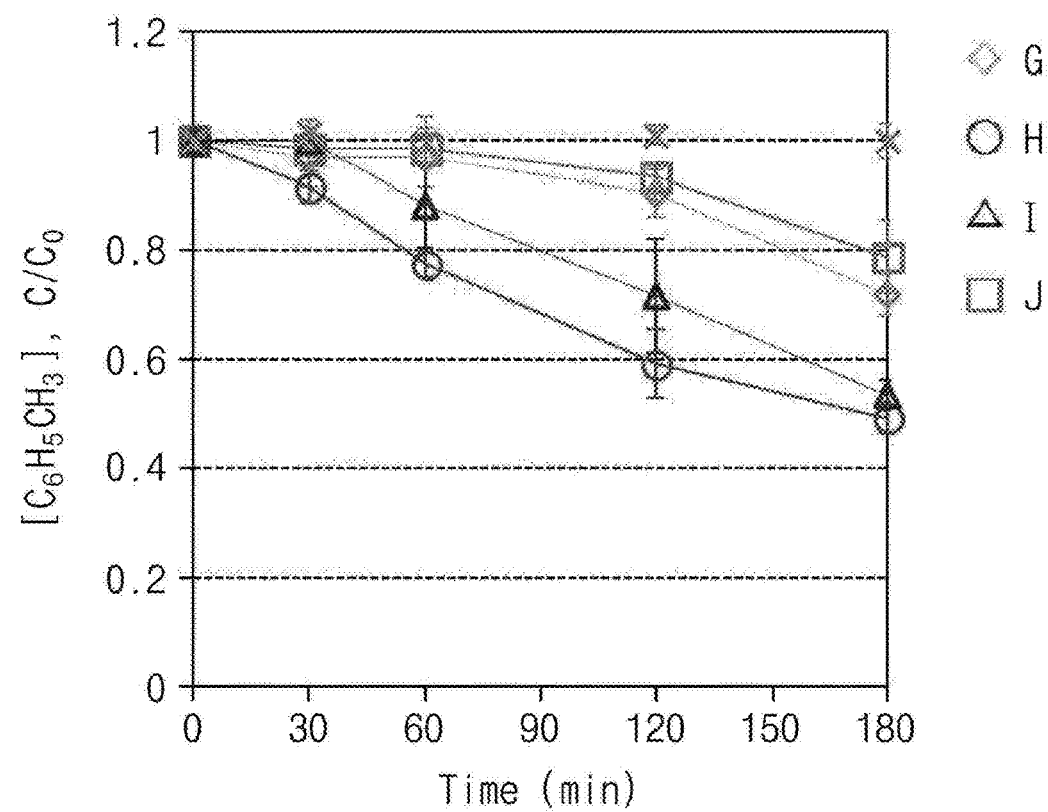
FIG. 15 is a graph showing a toluene removal rate according to time at low air flow rate conditions in a conventional fluid treatment apparatus.

FIG. 14 is a graph showing a toluene removal rate according to an air flow rate at low air flow rate conditions in a conventional fluid treatment apparatus, and FIG. 15 is a graph showing a toluene removal rate according to time at low air flow rate conditions in a conventional fluid treatment apparatus.

The fluid treatment apparatus used in FIGS. 14 and 15 have an opened inlet and do not include a separate guide member. The conventional fluid treatment apparatus includes substantially the same components as those shown in FIG. 6, except for the inlet of the housing and the guide member. In FIGS. 14 and 15, experiments were performed in a chamber of 1 m$^3$. A distance between the photocatalyst filter and the light source unit was about 20 mm, and three light sources that emit light of a wavelength band of about 365 nm were used. An average intensity of the ultraviolet light was about 20.0 mW/cm$^2$, and a size of the photocatalyst filter was 55 mm×55 mm×10 mm. The air flow rates of G, H, I, and J shown in FIGS. 14 and 15 corresponded to about 0.08 m$^3$/min, about 0.17 m$^3$/min, about 0.30 m$^3$/min, and about 0.41 m$^3$/min, respectively. Portions indicated by "X" in FIG. 15 show a case where the fluid treatment apparatus is not driven.

Referring to FIG. 14, the toluene was removed to a different degree depending on the air flow rate when the same fluid treatment apparatus was used under the low air flow rate conditions, however, there was no particular tendency. For example, the air flow rate increased in the order of G, H, I, and J, but the removal rate of toluene increased and then decreased again. Therefore, there was no significant relationship between the air flow rate and the toluene removal rate at the low air flow rate conditions. However, referring to FIG. 15, the removal efficiency of toluene was high when the fluid stayed in the fluid treatment apparatus for a longer time at the low air flow rate conditions, and it was confirmed that more fluid needs to stay in the fluid treatment apparatus for a long time through the above results.

Figure 16:
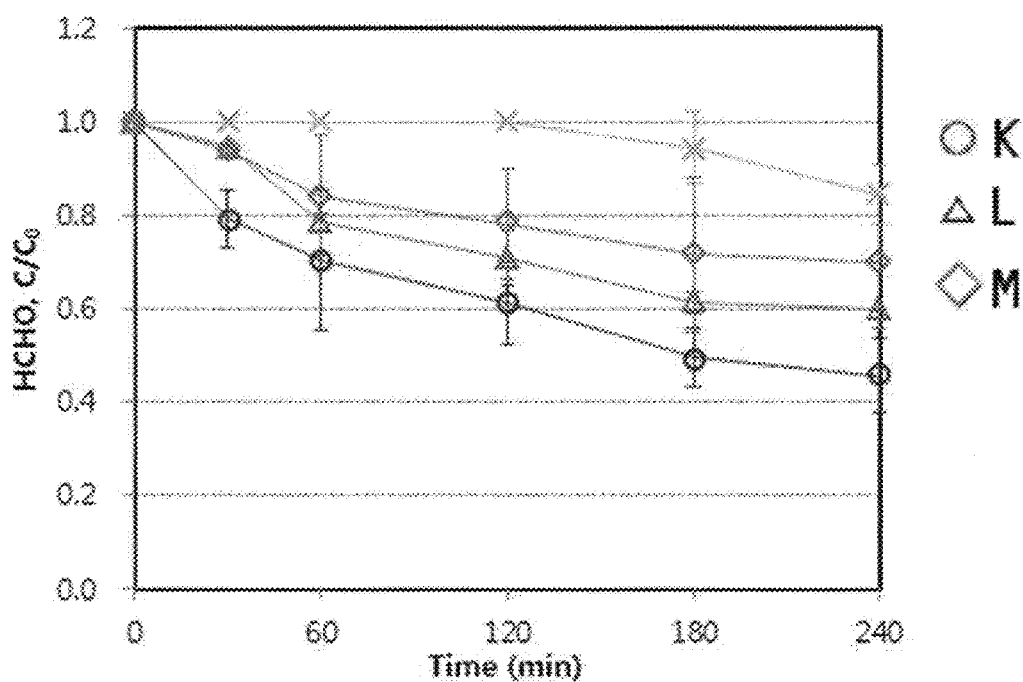
FIG. 16 is a graph showing a formaldehyde removal rate according to time at high air flow rate conditions in a conventional fluid treatment apparatus.

Table 1 shows a removal rate of formaldehyde with a time at high air flow rate conditions in the conventional fluid treatment apparatus, and FIG. 16 is a graph showing a formaldehyde removal rate according to the time at high air flow rate conditions in the conventional fluid treatment apparatus, which illustrates Table 1 as a graph.

TABLE 1

| Time (min) | Air flow rate | | |
| --- | --- | --- | --- |
| | 2.9 m³/min | 5.5 m³/min | 7.5 m³/min |
| 0 | — | — | — |
| 30 | 20.6 | 5.1 | 5.8 |
| 60 | 29.5 | 21.4 | 15.8 |
| 120 | 38.7 | 29.2 | 21.7 |
| 180 | 50.5 | 38.4 | 28.3 |
| 240 | 54.3 | 40.2 | 30.0 |

In Table 1 and FIG. 16, experiments were performed in a chamber of 4 m³. A distance between the photocatalyst filter and the light source unit was about 20 mm, and one light source that emits light of a wavelength band of about 365 nm was used. An average intensity of the ultraviolet light was about 20.5 mW/cm², and a size of the photocatalyst filter was 33 mm×33 mm×10 mm. The air flow rates of K, L, and M shown in FIG. 16 corresponded to about 2.9 m³/min, about 5.5 m³/min, and about 7.5 m³/min, respectively. Portions indicated by "X" in FIG. 16 shows a case where the fluid treatment apparatus is not driven. Referring to FIG. 16, as the air flow rate increased, the removal efficiency of formaldehyde relatively decreased with the passage of time at high air flow rate conditions. In particular, as the air flow rate increased from about 2.9 m³/min to about 5.5 m³/min, and then to about 7.5 m³/min, the removal rate of formaldehyde with the passage of time decreased. More particularly, when the air flow rate was about 2.9 m³/min, about 54% of formaldehyde was removed at a time point at which about 240 minutes elapsed, however, when the air flow rate was about 7.5 m³/min, only about 30% of formaldehyde was removed at the time point at which about 240 minutes elapsed.

Referring to FIG. 16, in the case of using the conventional fluid treatment apparatus at the high air flow rate conditions, the difference in the removal efficiency of formaldehyde according to the air flow rate was large. More particularly, it was observed that, as the air flow rate increased, the removal efficiency of formaldehyde reduced as the time during which the fluid stayed in the fluid treatment apparatus decreased. As such, it was observed that more fluid needs to be adjusted to stay in the fluid treatment apparatus for a sufficient time.

Figure 17:
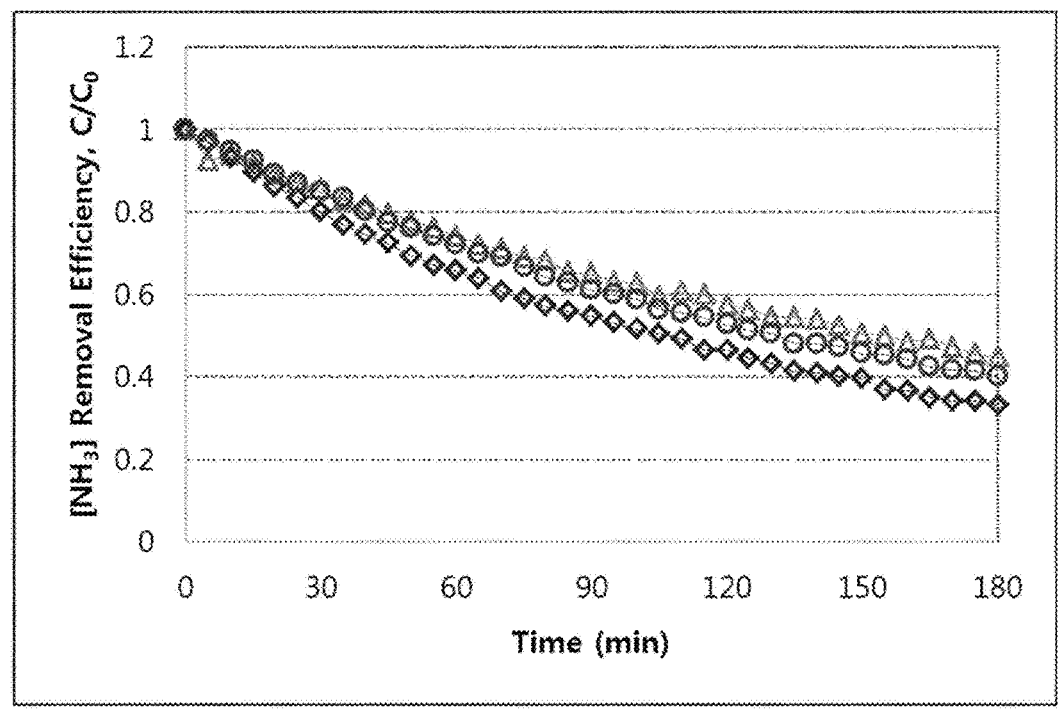
FIG. 17 and FIG. 18 are graphs respectively showing an ammonia removal rate and a formaldehyde removal rate of the fluid treatment apparatuses of FIGS. 6, 7, and 11 at low air flow rate conditions according to an exemplary embodiment.
Figure 18:
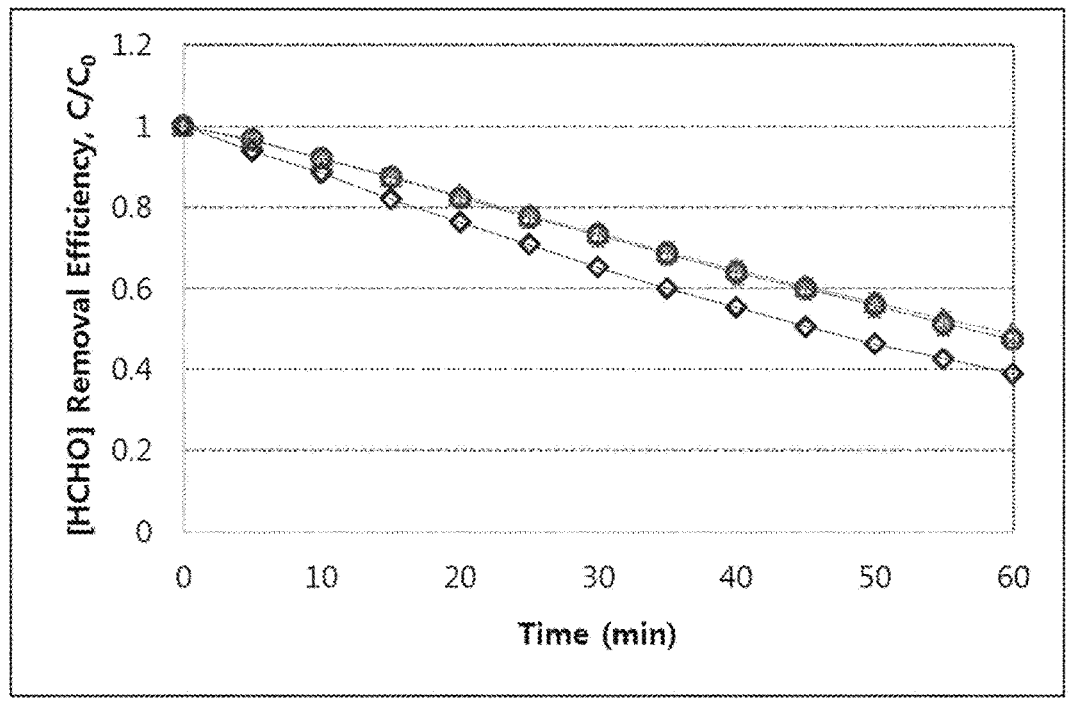

FIGS. 17 and 18 are graphs respectively showing an ammonia removal rate and a formaldehyde removal rate when using the fluid treatment apparatuses of FIGS. 6, 7, and 11 at low air flow rate conditions according to exemplary embodiments.

In FIGS. 16 and 17, experiments were performed under low air flow rate conditions (from about 0.01 m³/min to about 1 m³/min), and, in particular, the removal efficiency was measured while maintaining the air flow rate of about 0.2 m³/min. In FIGS. 16 and 17, the graph with lozenges (◇) is a result obtained when using the fluid treatment apparatus of FIG. 6, the graph with circles (○) is a result obtained when using the fluid treatment apparatus of FIG. 7, and the graph with triangles (Δ) is a result obtained when using the fluid treatment apparatus of FIG. 11.

As shown in FIGS. 16 and 17, under the low air flow rate conditions, the removal rate of ammonia and formaldehyde was higher in the case of using the fluid treatment apparatus shown in FIG. 6 than that in the case of using the fluid treatment apparatus of FIGS. 7 and 11. In particular, under the low air flow rate conditions, the removal rate of formaldehyde was higher when an angle between each slat and the direction perpendicular to the lower surface of the photocatalyst filter is an acute angle, and each slat was arranged in the direction closer to the lower surface of the photocatalyst filter along the advancing direction of the flow path when viewed from the cross-section than in the other cases. This means that the reaction time between the air and the photocatalyst filter was sufficiently ensured by moving more air to the photocatalyst filter at the low air flow rate conditions, and as a result, the deodorization efficiency of the fluid treatment apparatus was high.

Figure 19:
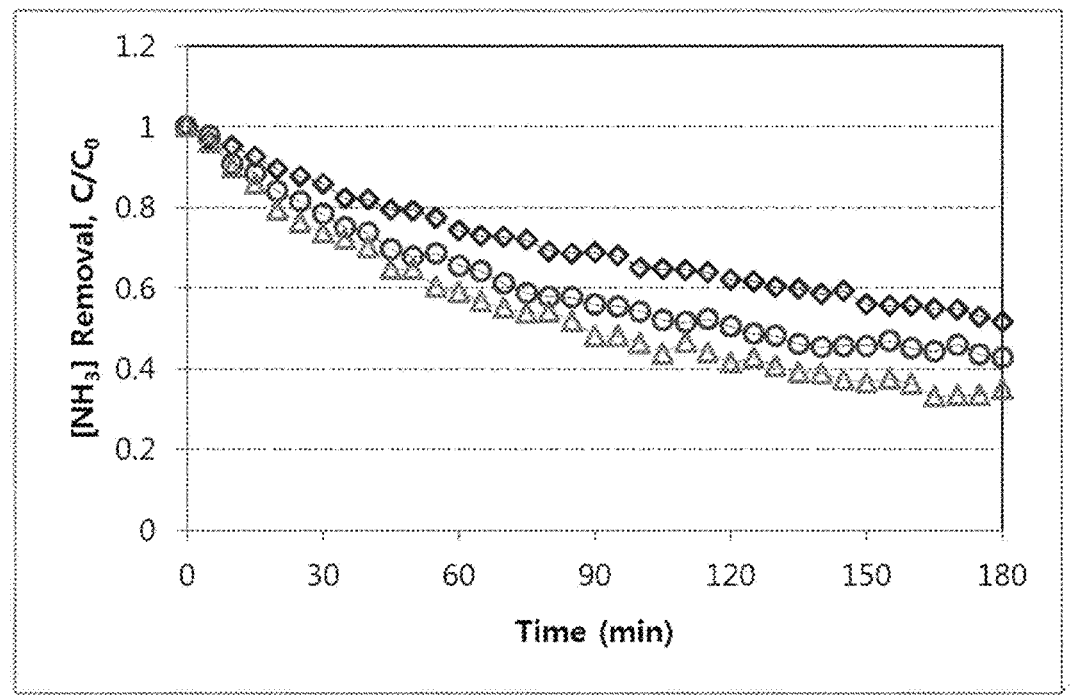
FIG. 19 and FIG. 20 are graphs respectively showing an ammonia removal rate and a formaldehyde removal rate of the fluid treatment apparatuses of FIGS. 6, 7, and 11 at low air flow rate conditions according to an exemplary embodiment.
Figure 20:
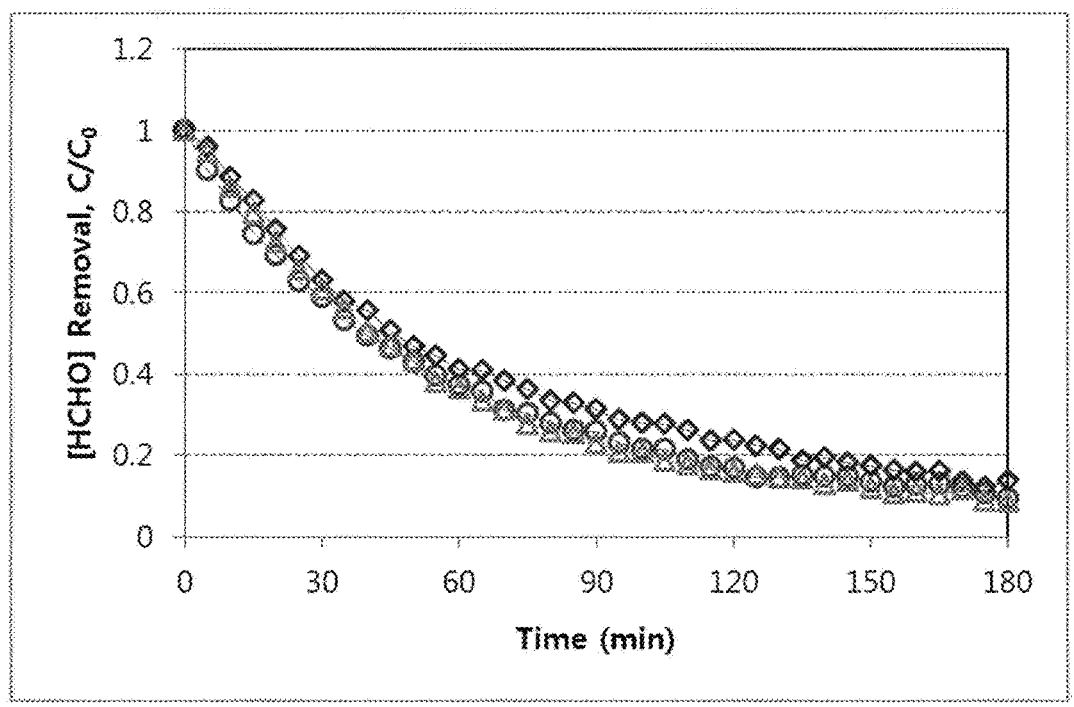

FIGS. 19 and 20 are graphs respectively showing an ammonia removal rate and a formaldehyde removal rate when using the fluid treatment apparatuses of FIGS. 6, 7, and 11 at low air flow rate conditions according to exemplary embodiments.

In FIGS. 19 and 20, experiments were performed under high air flow rate conditions (exceeding about 1 m³/min about 8 m³/min), and, in particular, the removal efficiency was measured while maintaining the air flow rate of about 4.7 m³/min. In FIGS. 19 and 20, the graph with lozenges (◇) is a result obtained when using the fluid treatment apparatus of FIG. 6, the graph with circles (○) is a result obtained when using the fluid treatment apparatus of FIG. 7, and the graph with triangles (Δ) is a result obtained when using the fluid treatment apparatus of FIG. 11.

As shown in FIGS. 16 and 17, under the high air flow rate conditions, the removal rate of ammonia and formaldehyde was higher in the case of using the fluid treatment apparatus shown in FIG. 7 than that in the case of using the fluid treatment apparatus of FIG. 6. In other words, under the high air flow rate conditions, the removal rate of ammonia and formaldehyde was higher when e an angle between each slat and the direction perpendicular to the lower surface of the photocatalyst filter is an obtuse angle, and each slat was arranged in the direction away from the lower surface of the photocatalyst filter along the advancing direction of the flow path when viewed from the cross-section than in the other cases. This means that the air with high flow velocity moved less to the photocatalyst filter under the high air flow rate conditions, and thus, the amount of air that passed the photocatalyst filter without reacting was reduced, and substantially simultaneously, the contact time of the photocatalyst filter with the air was maintained longer. As a result, the deodorization efficiency of the fluid treatment apparatus was high.

In addition, the removal rate of ammonia and formaldehyde was higher in the case of using the fluid treatment apparatus shown in FIG. 11 than that in the case of using the fluid treatment apparatuses of FIGS. 6 and 7. In the case of the fluid treatment apparatus shown in FIG. 11, the slats are perpendicular to the lower surface of the photocatalyst filter when viewed in a cross-section perpendicular to the lengthwise direction of the slats of the guide member. In this case, the air flows above the photocatalyst filter, the flow path of the air becomes longer than that in the case of FIGS. 6 and 7, and the flow rate decreases due to an increase in pressure loss. Thus, sufficient reaction of the air with the photocatalyst filter may be induced, and as a result, the deodorization efficiency may be enhanced.

As described above, considering FIGS. 19 and 20, it was observed that the degree of the reaction between the photocatalyst filter and the air is related to the movement direction of the air, as well as the air flow rate. According to an exemplary embodiment, the degree of reaction between the photocatalyst filter and the air may be maximized by setting the angle of the slats in the guide member by taking into account the degree of the air flow rate. More particularly, since the air treatment efficiency of the fluid treatment apparatus varies depending on the air flow rate and the air flow direction guided by the guide member, according to exemplary embodiments, the fluid treatment effect is maximized by setting the angle of the slats of the guide member to correspond to the predetermined air flow rate using the guide member.

The fluid treatment apparatus according to the exemplary embodiments may be used in various air conditioners of automobiles, refrigerators, and air cleaners.

According to exemplary embodiments, the fluid treatment apparatus may have improved fluid treatment efficiency and improved sterilization, purification, and deodorization efficiency.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A fluid treatment apparatus comprising:
a photocatalyst filter having a first surface and a second surface opposing the first surface;
a light source unit spaced apart from the photocatalyst filter to provide light to the first surface of the photocatalyst filter;
a housing including an inlet, an outlet, and a flow path formed between the inlet and the outlet and between the photocatalyst filter and the light source unit, the housing accommodating the photocatalyst filter and the light source unit; and
a guide member disposed at one side of the housing and including at least one slat to guide a movement direction of a fluid,
wherein all of the at least one slat is configured to be inclined at a first angle with respect to a first direction perpendicular to the first surface to be closer to the first surface of the photocatalyst filter along an advancing direction of the flow path when an air flow rate of the fluid has a first value, and inclined at a second angle greater than the first angle with respect to the first direction to be further away from the first surface of the photocatalyst filter along the advancing direction of the flow path when the air flow rate of the fluid is greater than the first value.

2. The fluid treatment apparatus of claim 1, wherein the slat is inclined in the direction away from the first surface along the advancing direction of the flow path when viewed in the cross-section.

3. The fluid treatment apparatus of claim 1, wherein the slat is inclined in the direction closer to the first surface along the advancing direction of the flow path when viewed in the cross-section.

4. The fluid treatment apparatus of claim 1, wherein the slat is provided in a plural number, and at least one of the slats forms an angle with the first surface that is different from those formed by the remaining slats with the first surface.

5. The fluid treatment apparatus of claim 1, wherein the slat is concavely curved with respect to the first surface when viewed in the cross-section.

6. The fluid treatment apparatus of claim 1, wherein the slat is convexly curved with respect to the first surface when viewed in the cross-section.

7. The fluid treatment apparatus of claim 1, further comprising an angle adjusting member to adjust an angle of the slat with respect to the first surface.

8. The fluid treatment apparatus of claim 7, wherein the angle is adjusted by the angle adjusting member depending on the air flow rate of the fluid introduced through the inlet.

9. The fluid treatment apparatus of claim 1, wherein the slat extends in one direction, a lengthwise direction of the slat is perpendicular to a direction of the flow path, and a widthwise direction of the slat is parallel to the direction of the flow path.

10. The fluid treatment apparatus of claim 9, wherein the lengthwise direction of the slat is parallel to the first surface.

11. The fluid treatment apparatus of claim 1, wherein the flow path is parallel to or inclined with respect to the first surface.

12. The fluid treatment apparatus of claim 1, wherein the housing comprises:
a ceiling portion on which the photocatalyst filter is mounted;
a bottom portion on which the light source unit is mounted; and
a sidewall portion connecting the ceiling portion and the bottom portion.

13. The fluid treatment apparatus of claim 12, wherein the sidewall portion of the housing includes an insertion groove into which the photocatalyst filter is slide-coupled.

14. The fluid treatment apparatus of claim 1, wherein the light source unit comprises at least one light source configured to emit light having a wavelength band of at least one of an ultraviolet light and a visible light.

15. The fluid treatment apparatus of claim 14, wherein the light source unit emits light having an ultraviolet C wavelength band.

16. The fluid treatment apparatus of claim 1, wherein the fluid treatment apparatus is configured to be mounted on an air conditioner of an automobile, a refrigerator, or an air cleaner.

17. The fluid treatment apparatus of claim 1, wherein the guide member is provided integrally with the housing without being separated from the housing.

18. An air conditioner comprising:
an air-conditioning case;
a heat exchanger disposed in the air-conditioning case; and
a fluid treatment apparatus disposed in the air-conditioning case, the fluid treatment apparatus comprising:
a photocatalyst filter having a first surface and a second surface opposing the first surface;
a light source unit spaced apart from the photocatalyst filter to provide light to the first surface of the photocatalyst filter;

a housing including an inlet, an outlet, and a flow path formed between the inlet and the outlet and between the photocatalyst filter and the light source unit, the housing accommodating the photocatalyst filter and the light source unit; and
a guide member disposed at one side of the housing and including at least one slat to guide a movement direction of a fluid, wherein all of the at least one slat is configured to be inclined at a first angle with respect to a first direction perpendicular to the first surface to be closer to the first surface of the photocatalyst filter along an advancing direction of the flow path when an air flow rate of the fluid has a first value, and inclined at a second angle greater than the first angle with respect to the first direction to be further away from the first surface of the photocatalyst filter along the advancing direction of the flow path when the air flow rate of the fluid is greater than the first value.

19. The air conditioner of claim 18, further comprising an angle adjusting member configured to control an angle of the slat with respect to the first surface depending on the air flow rate of the fluid introduced through the inlet.

* * * * *